US008879063B2

(12) United States Patent
Bernhard

(10) Patent No.: US 8,879,063 B2
(45) Date of Patent: Nov. 4, 2014

(54) MEASURING SYSTEM FOR MEASURING ABSORPTION OR SCATTERING AT DIFFERENT WAVELENGTHS

(75) Inventor: Ralf Bernhard, Stuttgart (DE)

(73) Assignee: Endress + Hauser Conducta Gesellschaft fur Mess- Und Regeltechnik mbH + Co. KG, Gerlingen (DE)

( * ) Notice: Subject to any disclaimer, the term of this patent is extended or adjusted under 35 U.S.C. 154(b) by 245 days.

(21) Appl. No.: 13/302,056

(22) Filed: Nov. 22, 2011

(65) Prior Publication Data

US 2012/0133935 A1    May 31, 2012

(30) Foreign Application Priority Data

Nov. 26, 2010  (DE) .......................... 10 2010 062 015

(51) Int. Cl.
*G01N 21/00* (2006.01)
*G01N 21/31* (2006.01)
*G01N 21/51* (2006.01)

(52) U.S. Cl.
CPC ................ *G01N 21/51* (2013.01); *G01N 21/31* (2013.01)
USPC ........................................................ 356/338

(58) Field of Classification Search
None
See application file for complete search history.

(56) References Cited

U.S. PATENT DOCUMENTS

| | | | |
|---|---|---|---|
| 3,910,701 A | 10/1975 | Henderson | |
| 5,317,162 A * | 5/1994 | Pinsky et al. | ................. 356/317 |
| 5,492,118 A * | 2/1996 | Gratton et al. | ................. 356/338 |
| 5,855,205 A * | 1/1999 | Papaionnou | ................. 356/477 |
| 5,983,121 A * | 11/1999 | Tsuchiya | ................. 356/432 |
| 6,488,892 B1 * | 12/2002 | Burton et al. | ................. 356/246 |
| 7,428,434 B2 * | 9/2008 | Tromberg et al. | ............. 356/337 |
| 2007/0256475 A1 | 11/2007 | Crane | |
| 2009/0012721 A1 * | 1/2009 | Kimura et al. | ............. 250/459.1 |
| 2010/0045991 A1 | 2/2010 | Miklos | |

FOREIGN PATENT DOCUMENTS

| | | |
|---|---|---|
| AT | 504 436 B1 | 5/2008 |
| DE | 41 06 042 A1 | 8/1991 |
| DE | 200 12 060 U1 | 11/2000 |
| DE | 10 2009 011 421 B3 | 4/2010 |
| EP | 0 026 046 A1 | 4/1981 |

* cited by examiner

*Primary Examiner* — Tarifur Chowdhury
*Assistant Examiner* — Juan D Valentin, II
(74) *Attorney, Agent, or Firm* — Bacon & Thomas, PLLC

(57) ABSTRACT

A measuring system for measuring absorption or scattering of a medium at a plurality of different wavelengths, whereby the measurements for the different wavelengths are performable as simultaneously and as accurately as possible. The measuring system comprises: a measuring chamber; a transmitting unit, which sends light of its respective wavelength into the measuring chamber; a control, which operates each light source with a different time modulation of transmission intensity for each wavelength; a detector for measuring a total radiation intensity. The total radiation intensity corresponds to a superpositioning of each intensity portion striking the detector for each wavelength; and a signal processing system, which determines for each of the wavelengths the associated intensity portion based on the total radiation intensity measured by detector and the modulations.

10 Claims, 4 Drawing Sheets

MEASURING SYSTEM FOR MEASURING ABSORPTION OR SCATTERING AT DIFFERENT WAVELENGTHS

TECHNICAL FIELD

The invention relates to a measuring system for measuring absorption or scattering of a medium at a plurality of different wavelengths.

The measuring system comprises a measuring chamber for accommodating the medium, a transmitting unit, which sends light of different wavelengths into the measuring chamber, a detector for measuring radiation portion intensities, which are dependent on the absorption or the scattering in the medium and which emerge from the measuring chamber at the site of the detector at the individual wavelengths. The radiation portion intensities, in the case of a detector arranged downstream from the measuring chamber in the transmission direction, are a direct measure for the absorption in the medium, and, in the case of a detector arranged at a predetermined scatter angle downstream from the measuring chamber in the transmission direction, a direct measure for the scattering of light that occurred in the medium at this scatter angle.

The radiation portion intensities, in the case of a detector arranged downstream from the measuring chamber in the transmission direction, are a direct measure for the absorption in the medium, and, in the case of a detector arranged at a predetermined scatter angle downstream from the measuring chamber in the transmission direction, a direct measure for the scattering of light that occurred in the medium at this scatter angle.

BACKGROUND DISCUSSION

Measuring systems for measuring absorption or scattering of a medium are applied today in a large number of industrial applications, especially in chemistry and biochemistry as well as in water analysis, both for measuring taken samples as well as for on-line measurement of scattering or absorption. In measuring samples, the measuring chamber regularly comprises a cuvette fillable with a sample of the medium; the measuring chamber is inserted in the measuring system and is irradiated through correspondingly placed windows in the measuring system. In measuring on-line, the measuring system is embodied, for example, as a probe, which is placed in the medium. Here the measuring chamber is formed by a cavity in the probe, which is filled by the medium, and is irradiated through windows mounted on the external sides of the cavity.

In both absorption measuring as well as in scattering measuring, a transmitting unit is applied, which radiates light in a predetermined transmission direction into the measuring chamber through an entrance surface, and a detector is provided, which measures a radiation intensity, which is dependent on the absorption or scattering, emerging from the measuring chamber through an exit surface. Absorption and scattering measurement systems only differ by the number and positioning of the detectors. In absorption measuring, measurements are made in the transmission direction, i.e. only one detector is required, which is arranged downstream from an exit surface, in the main transmission direction, where the exit surfaces lies opposite the entrance surface.

In contrast, in scattering measuring, measurements are made at one or a plurality of predetermined scattering angles from the predetermined transmission direction. Here the detectors are located downstream from exit surfaces arranged at predetermined scattering angles from the transmission direction.

Described in DE 41 06 042 A1 is a measuring system for measuring low light absorptions at a single predetermined wavelength, subsequently to be referenced herein as the measuring wavelength. For this, a monochromatic measuring beam, whose light has the predetermined measuring wavelength, is sent through the medium. Additionally, a monochromatic reference beam is sent through the medium; the reference beam, which has a wavelength subsequently referred to herein as the reference wavelength, which has a value, for which the medium is transparent. In order to be able to measure small absorptions, here both a measurement radiation intensity, which has the measuring wavelength, emerging from the medium as well as a reference radiation intensity, which has the reference wavelength, emerging from the medium are measured, and the associated measurement and reference signals representing the measuring and reference radiation intensity are subjected to a direct, analog subtraction. In such case, a reference measurement is executed on a reference medium in advance; with the reference measurement, an intensity difference related to the measuring system between the measuring radiation intensity and the reference radiation intensity is first determined based on the difference. This intensity difference is compensated in the following measurement operation optically using a tunable gray filter or electronically using a corresponding weighting in the subtraction. In the following measurement operation, a quick, exact measuring of small absorptions is executed based on the difference between the measurement signal and reference signal automatically considering the intensity difference related to the measuring system. In this way, the measuring resolution is increased, since the resolution range comprises here only the order of magnitude of the difference, but not the essentially larger order of magnitude of the individual variables.

For this, the measuring beam and reference beam are sent simultaneously through the medium, and the total radiation emerging from the medium is fed via a filter matched to the measuring wavelength to a first detector, which measures the measurement radiation intensity of the measuring wavelength penetrating through the medium, and is fed via a second filter matched to the reference wavelength to a second detector, which measures the reference radiation intensity of the reference wavelength penetrating through the medium.

Alternatively, the production of a measurement beam and reference beam of different wavelengths by two different laser diodes is described; the measurement beam and reference beam are controlled mechanically by a chopper installed in the beam path or controlled electrically by an alternating current operation of the laser diodes; the measurement beam and reference beam are sent through the medium in rapid alternation. Another embodiment provides alternately clocking the measurement and reference beams with a first frequency and supplementally the reference beam with a second frequency by means of a chopper. In both cases all radiation intensities can be registered with a single detector, and therefrom the measurement radiation intensity and the reference radiation intensity are determined based on the two frequencies with which the measurement beam and reference beam are clocked one after the other by means of lock-in amplification technology.

There are a large number of applications, in which measurements with different wavelengths are required. An example of this is the measurement of absorption in the optical region, where, for example, color changes of reagent solutions are detected or monitored.

Current measuring systems applied for this comprise light sources, especially LEDs, of different wavelength, in which each is individually operated successively one after the other for a predetermined measurement duration. This offers the advantage that only one measuring detector is required for measuring the radiation intensity striking thereon, and a spectrometric splitting and analysis of the radiation emerging from the measuring chamber as well as an optical filter can be omitted. An example of this is described in U.S. Pat. No. 3,910,701.

Relatively large intensity jumps occur on the detector side by successively turning the individual light sources on and off; the intensity jumps are difficult to process both by the detector, e.g. a photodiode, as well as electronics following the detector, especially amplifier circuits for the amplification of the measurement signal of the detector. Since the amplifier circuit must be able very rapidly to accommodate the amplitude jumps of the detector signal, a high quality, fast amplifier is required. Fast amplifiers are, however, as a rule, very sensitive to electromagnetic disturbing influences, such as e.g. disturbance fields caused by motors or switching controllers. Due to the sensitivity of the amplifier, a crosstalk of electromagnetic disturbance fields from the transmitter to the amplifier circuit can also occur.

Moreover, hard switching events produce harmonic waves, which unavoidably occur in turning the operated light sources on and off one after the other; the harmonic waves can only be filtered out from the detector signal with difficulty.

A difference building between radiation intensities measured at different wavelengths following one another, as applied in the state of the art mentioned above, where the measuring occurs based on the difference between the measurement and reference signal, would indeed be suitable to reduce disturbances produced by switching events under certain circumstances; however, it cannot be applied here since the absolute values of the successively measured radiation intensities of the individual wavelengths are required.

Correspondingly, switching events are preferably reduced to a minimum, in that the duration of transmission times, in which one of the light sources transmits, is selected to be as large as possible. Transmission time durations of a tenth of a second and more are, consequently, no rarity. This is, however, especially problematic in measuring systems with many light sources of different wavelength, since a measuring cycle, in which the absorption or scattering of the individual different wavelengths is successively measured one after the other, requires a very long time. With ten different wavelengths, the duration of a complete measuring cycle would already be 1 second. Disturbances, such as e.g. air bubbles arising in the ray path for a short time, dust particles or other types of impurities in the medium, occurring for a short time in the medium correspondingly influence only the active partial measurements of the measuring cycle during the occurrence of these disturbances. In such case, each partial measurement affected by the disturbances arising in the medium for a short time, depending on the type of disturbance, measures a much too high or much too low radiation intensity. This can lead to drastically defective measurements. Absorption measurements for monitoring a color change of a medium, e.g. from red to green, are an example of this. If an air bubble occurs in the medium during the absorption measurement with the red light source and has already disappeared in the following measuring with the green light source, then a statement concerning the color change can no longer be made based on the ratio of the red transmission intensity to the green transmission intensity.

In measuring systems, which permanently operate a single monochromatic or multi-colored light source and measure the total radiation intensity penetrating through the medium, disturbances occurring in the medium for a short time can subsequently be recognized based on the associated sudden rises or declines in the measured radiation intensity, and at least the measurement results achieved in these periods of time are discarded. This is practically no longer possible with successive measurements with different wavelengths since a disturbance occurring in the medium for a short time here only affects individual measurement portions.

A shortening of the transmission times of the successively operated light sources would effect an improvement here in two ways. On the one hand, the period of time is shortened in which the short time disturbance has a disadvantageous affect. With long transmission times, short time disturbances, whose duration is shorter than the transmission time, corrupt the integral measurement over the entire transmission time interval. The shorter the transmission time is, the shorter the lasting negative influence of the disturbance over the duration of the disturbance. On the other hand, short time disturbances, which last clearly longer than the short transmission times, affect a number of partial measurements following one another and can therefore be subsequently recognized more easily.

SUMMARY OF THE INVENTION

A shortening of the transmission times is, however, unavoidably connected with the disadvantages described above.

It is an object of the invention to provide a measuring system for measuring absorption or scattering of a medium at different wavelengths, where the measurements at different wavelengths are performable with the measuring system as simultaneously and accurately as possible.

For this, the invention resides in a measuring system for measuring absorption or scattering of a medium at a plurality of different wavelengths, comprising:

A measuring chamber for accommodating the medium;
a transmitting unit,
   which has, for each wavelength, an electrically controllable light source, which sends light of its respective wavelength into the measuring chamber in measurement operation;
a control,
   which operates each light source with a different time modulation of the transmission intensity for each wavelength;
a detector for measuring a total radiation intensity dependent on the modulations and the absorption or scattering in the medium and emerging from the measuring chamber at the site of the detector; the total radiation intensity corresponds to a superpositioning of each intensity portion striking the detector for each wavelength; and
a signal processing system,
   which determines for each wavelength the associated intensity portion based on the total radiation intensity measured by the detector and the modulations.

In a further development, each of the light sources transmits light of its wavelength into the measuring chamber during predetermined transmission times with the time curve of the modulation used for its wavelength, and the transmission times of the light sources of different wavelength overlap in time.

In an additional further development, the different modulations for the individual wavelengths have time curves such that on average, an at least approximately constant number of light sources simultaneously send light into the measuring chamber in measurement operation at any given time.

In a first variant, the modulations are periodic modulations with predetermined different frequencies for the individual wavelengths.

In a further development of the first variant, the modulations have continuous time curves, especially sinusoidal time curves.

In an additional further development of the first variant, the signal processing system determines the intensity portions based on amplitudes of a Fourier transform of the measured radiation intensity arising from the predetermined frequencies for the particular wavelength.

In a second variant of the invention, the modulations are non-periodic modulations, especially randomly generated modulations.

In a further development of the second variant,
the signal processing system has for each of the wavelengths a filter,
which filters from a measurement signal representing the measured radiation intensity a fraction correlating with the time curve of the modulation for the particular wavelength; and
the signal processing system determines the associated intensity portion for this wavelength based on the respective fraction.

In an embodiment of the invention,
a transmission optics is provided, via which the light of the light sources is sent into the measuring chamber along a predetermined transmission direction on a spatially limited measuring path; and/or
a receiving optics is provided, which focuses light escaping from the measuring chamber onto the detector.

The invention has the advantage that all light sources corresponding to the predetermined modulations for the particular wavelengths can be operated virtually simultaneously, since the intensity portions arising with the individual wavelengths are derivable from the total radiation intensity measured by the detector based on the predetermined modulation for each wavelength. Via a corresponding specification of the modulations, it can thereby be assured that, on average, at least an approximately constant number of light sources simultaneously sends light into the measuring chamber at any time. In this way, drastic fluctuations of the radiation intensity striking the detector are prevented. Correspondingly, very rapid or high frequency modulations can also be applied without high quality fast and disturbance sensitive amplifier circuits being required.

Fast or high frequency modulations offer the advantage that disturbances occurring in the medium for a short time effect a marked rise or decline of a plurality or even all measured intensity portions for the individual wavelengths, and, thus, can be subsequently recognized and the associated measurement results can be discarded. This is also naturally analogously true for the total radiation intensity measured by the detector.

Moreover, disturbances occurring in the medium for a short time can also be recognized with the application of slower or low frequency modulations based on the total radiation intensity measured by the detector, to the extent that via the modulation it is assured that at least an approximately constant number of light sources simultaneously sends light into the measuring chamber at any time. A disturbance occurring in the medium for a short time also effects a corresponding fall or rise of the total measured radiation intensity.

BRIEF DESCRIPTION OF THE DRAWINGS

The invention and other advantages will now be explained in greater detail based on the figures of the drawing, in which two examples of embodiments are presented. Equal elements are provided in the figures with equal reference characters. The figures of the drawing show as follows.

DETAILED DISCUSSION IN CONJUNCTION WITH THE DRAWINGS

Figure 1:
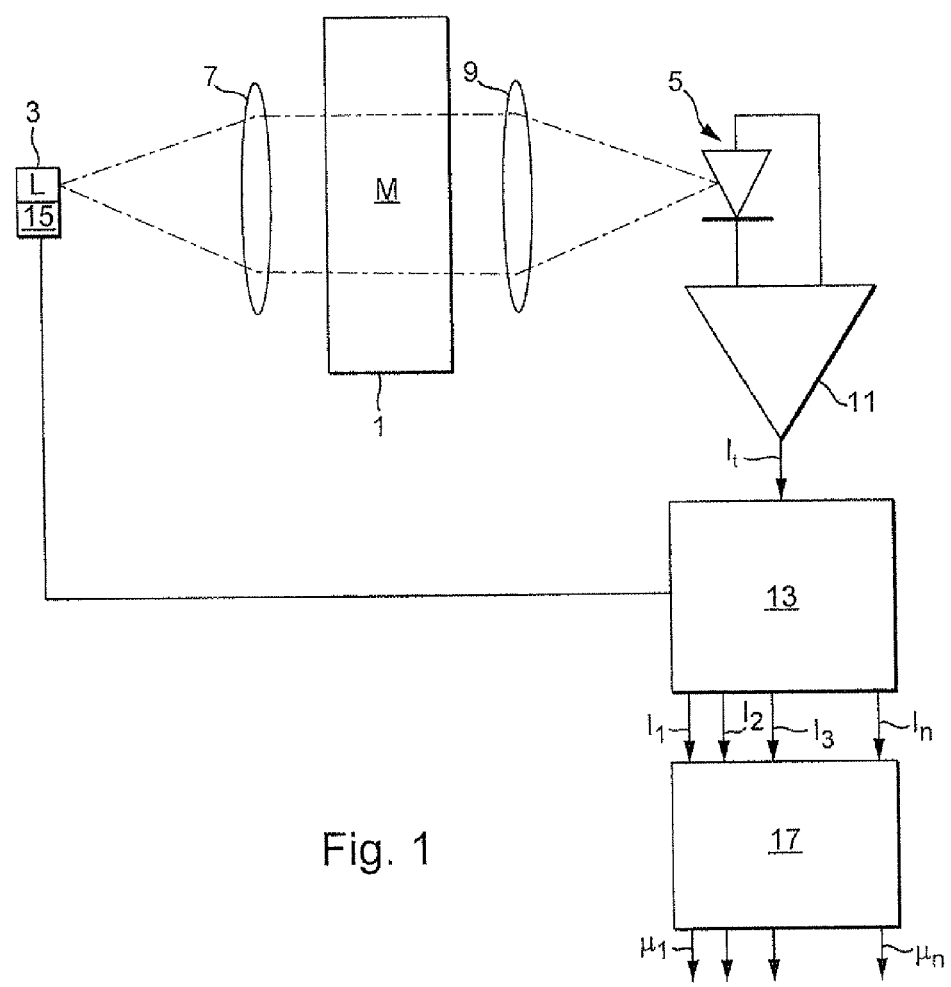
FIG. 1 is an absorption measurement system of the invention.

FIG. 1 shows as an example a measuring system of the invention as an absorption measurement system for measuring the absorption of a medium M at a plurality of different wavelengths $\lambda$.

The measuring system comprises a measuring chamber 1 for accommodating medium M. As already described above, measuring chamber 1 is, for example, a cuvette fillable with a sample of medium M, inserted in the measuring system. Alternatively, the measuring system can be embodied as a probe, which is placed in medium M. In this case measuring chamber 1 is formed by a cavity, which is filled by medium M, in the probe.

A transmitting unit 3, subsequently described in detail, is provided; transmitting unit 3 sends light into measuring chamber 1 in measurement operation, and a single detector 5 is provided, which serves to measure a total radiation intensity $I_t$ emerging from measuring chamber 1 at the site of detector 5. The measuring of the absorption occurs in the direction of transmission. I.e. detector 5 is arranged here on a side of measuring chamber 1 lying opposite transmitting unit 3 behind measuring chamber 1 in the transmission direction. The light of transmitting unit 3 is preferably sent through measuring chamber 1 on a predetermined, spatially limited measuring path, shown here by dashed lines; the measuring path is as narrow as possible. This offers the advantage that light of different wavelengths take the same path through medium M, and are thereby exposed to the same conditions in medium M. For this, a transmission optics 7, here shown schematically as a lens, can be provided on the transmission side between transmitting unit 3 and measuring chamber 1; transmission optics 7 effects a homogeneous parallel beam guidance of the light with a small beam cross section along the measuring path.

Additionally, a receiving optics 9, shown schematically as a lens, can likewise be provided here on the receiving side; receiving optics 9 focuses the light emerging from measuring chamber 1 via the measuring path onto detector 5.

Detector 5—as presented here—is a photodiode, for example. Alternatively, however, solar cells or photosensitive field effect transistors can also be applied as detectors. Optical filters and expensive spectral analyzers can be completely omitted due to the invention.

Detector 5 produces an output signal, here an output voltage, which shows the total radiation intensity $I_t$ striking detector 5. The output signal is fed to an amplifier circuit 11, illustrated here as an amplifier, which amplifies the output signal and feeds the measurement signal reflecting the total radiation intensity $I_t$ striking detector 5 to a signal processing system 13 connected thereto.

Transmitting unit 3 comprises an electrically controllable light source $L_1, \ldots L_n$ for each of the wavelengths $\lambda_1, \ldots \lambda_n$ for which the absorption is measured; light source $L_1, \ldots L_n$ serves to transmit light of such wavelength $\lambda_1, \ldots \lambda_n$ into measuring chamber 1. Electrically controllable LEDs, for example, can be used as light sources L. A light source L can naturally also comprise a number of synchronously controlled transmitting elements, e.g. a number of LEDs.

According to the invention, a control 15 is provided; control 15 operates the individual light sources $L_1, \ldots L_n$ with different time modulations of their transmission intensities $I_{01}, \ldots I_n$ for each individual wavelength $\lambda_1, \ldots \lambda_n$. The total radiation intensity $I_t$ striking detector 5, is, thus, a superpositioning, which is dependent on the different modulations and the absorption in medium M, of intensity portions $I_1, \ldots I_n$ each having only one of the wavelengths $\lambda_1, \ldots \lambda_n$ striking detector 5. Signal processing system 13 is connected to control 15, and determines the associated intensity portions $I_1, \ldots I_n$ based on the total radiation intensity $I_t$ measured by detector 5 and the wavelength specific modulations for each of the wavelengths $\lambda_1, \ldots \lambda_n$.

A measuring electronics 17, which determines the absorption $\mu_1, \ldots \mu_n$ of the medium for the individual wavelengths $I_1, \ldots I_n$, based on the intensity portions $I_1, \ldots I_n$ determined by signal processing system 13, is connected to signal processing system 13, and provides a display and/or additional processing. The determination of the absorption occurs based on the exponential relationship between the radiation intensity $I_1, \ldots I_n$ (which is related to the radiation intensity $I_{01}, \ldots I_{0n}$ sent) emerging from the medium M and the product of the absorption $\mu_1, \ldots \mu_n$ for each respective wavelength $\lambda_1, \ldots \lambda_n$ and distance traveled in medium M. This is the case with conventional absorption measuring devices and, consequently, such is not described in more detail here.

The time modulations of the radiation intensities $I_{01}, \ldots I_{0n}$, with which the individual light sources $L_1, \ldots L_n$ transmit, can have, according to a first variant of the invention, a periodic curve or, according to a second variant of the invention, a non periodic curve, especially a randomly generated curve. It is only absolutely required that the modulations for the different wavelengths $\lambda_1, \ldots \lambda_n$ with which the absorption in the medium should be measured, are different. In such case, each modulation has a cross correlation to all other modulations that is as low as possible, ideally a cross correlation of zero.

Preferably, the different modulations have a time curve, in which the transmission times, in which the individual light sources L transmit light with the respective wavelengths $\lambda$, overlap in time. This has the effect that the total radiation intensity $I_t$ striking detector 5 is always composed of at least two non-zero intensity portions, and, thus, it is thereby assured in normal operation that the intensity does not sink to a minimum. Preferably, modulations are applied, which have a time curve, in which, on average, at least an approximately constant number of light sources $L_1, \ldots L_n$ simultaneously send light into measuring chamber 1 in measurement operation at any time.

In this way, drastic fluctuations or jumps of the radiation intensity striking detector 5 arising, as in the state of the art mentioned above, from the successive or alternating operation of individual light sources or from the connected hard turning off and on of individual light sources, are prevented.

Moreover, the value range of the radiation intensity to be measured, for which detector 5 and the subsequent electronics, especially amplifier circuit 11, is to be designed, can be markedly reduced via a targeted overlapping of the transmission times.

Both the prevention of drastic intensity fluctuations and intensity jumps as well as the limitation of the value range clearly enable the use of fewer, slower and less sensitive amplifier circuits 11, which are accordingly not only more cost effective, but also markedly less sensitive to disturbing electromagnetic radiation penetrating from the exterior.

Figure 2:
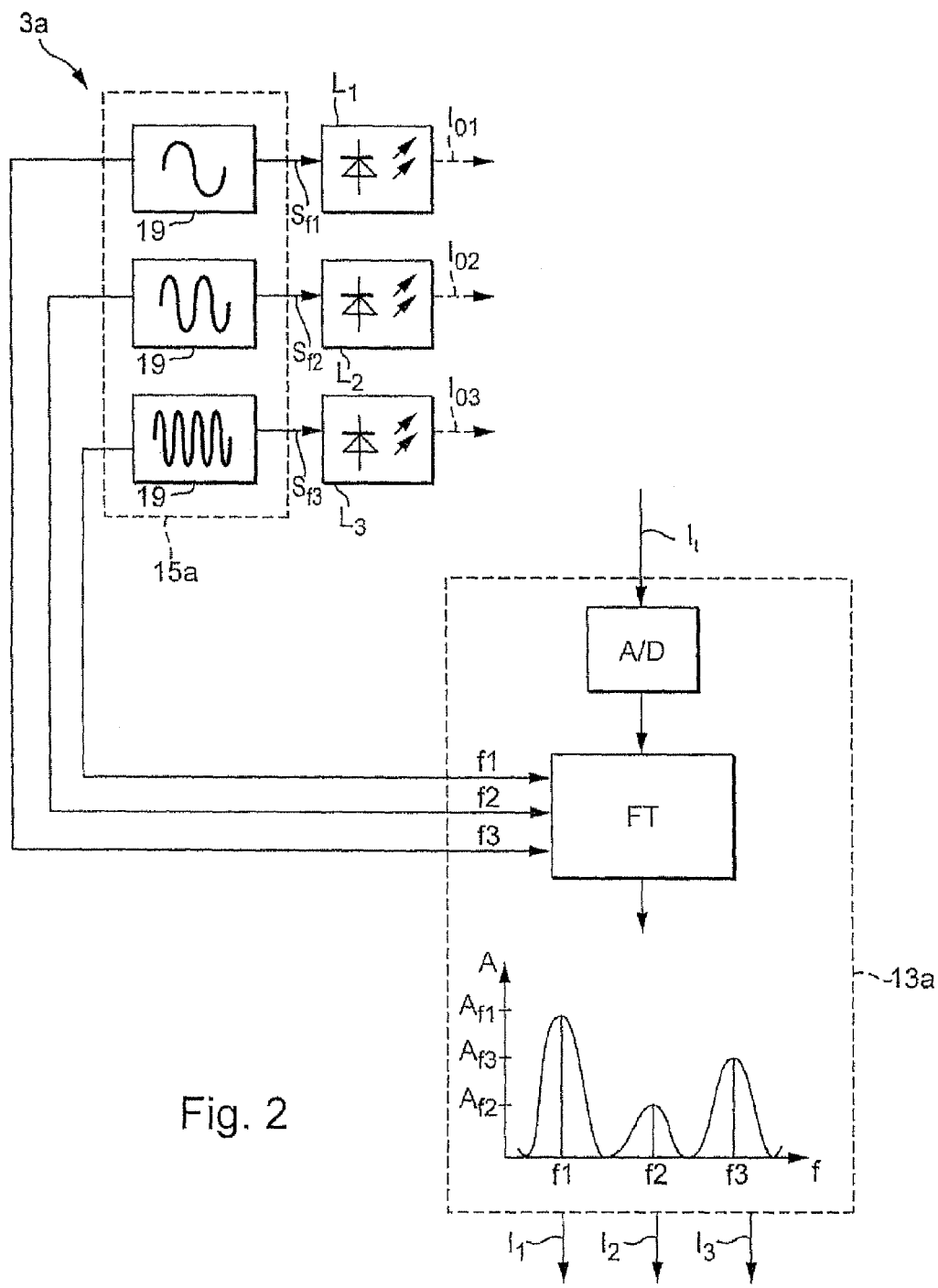
FIG. 2 is a transmission system and a signal processing system for an absorption measurement system according to FIG. 1 using periodic modulation of the light sources.

FIG. 2 shows an example of an embodiment of the first variant of the invention with periodic modulation of light sources L. Only the correspondingly embodied transmitting unit 3a, the associated control 15a, as well as the associated signal processing system 13a connected to amplifier circuit 11 of FIG. 1 are shown here. The remaining components can be assumed to be identical to those in FIG. 1. By way of example, three light sources $L_1, L_2, L_3$ are shown; light source $L_1$ sends light of wavelength $\lambda_1$, the light source $L_2$ sends light of wavelength $\lambda_2$, and the light source $L_3$ sends light of wavelength $\lambda_3$, through measuring chamber 1. The radiation intensities. $I_{01}, I_{02}, I_{03}$, with which light sources $L_1, L_2, L_3$ transmit light of each wavelength $\lambda_1, \lambda_2, \lambda_3$, are time modulated by means of control 15a. Control 15a comprises for this purpose three modules 19, each connected to a light source $L_1, L_2, L_3$. Each module 19 produces a control signal $S_{f1}, S_{f2}, S_{f3}$ with a predetermined frequency $f_1, f_2, f_3$ with which the radiation intensity $I_{01}, I_{02},$ or $I_{03}$ of each light source $L_1, L_2, L_3$ connected thereto is periodically modulated. The three frequencies $f_1, f_2, f_3$ are different from one another, and preferably lie outside the frequency ranges of possible disturbance signals. Disturbance signals in this sense are e.g. electrical disturbance signals in the region of 50 Hz that can arise e.g. through grid hum, or optical disturbance signals, such as e.g. stray light transmitted from luminescent lamps arranged in the environment.

Preferably, the processing of the amplified measurement signal representing the total radiation intensity $I_t$ striking detector 5 is digital. For this, the measurement signal is digitized in an analog/digital converter A/D integrated in signal processing system 13a or connected in front of signal processing system 13a.

Signal processing system 13a then determines the associated intensity portions $I_1, I_2, I_3$ based on the predetermined modulations for the individual wavelengths $\lambda_1, \lambda_2, \lambda_3$ and the measurement signal. In the case of periodic modulations with predetermined different frequencies $f1_1, f_2, f_3$, this can occur, for example, via a Fourier transformation of the measurement signal. This can be executed, for example, by a microprocessor, here marked FT, equipped with corresponding software. From this, the amplitudes $A_{f1}, A_{f2}, A_{f3}$ of the Fourier-transformed measurement signal with the predetermined different frequencies $f_1, f_2, f_3$ of the individual modulations are preferably likewise determined by means of the microprocessor FT. Since the ratio of the amplitudes $A_{f1}, A_{f2}, A_{f3}$ of the Fourier-transformed measurement signal at the predetermined different frequencies $f_1, f_2, f_3$ corresponds to the ratio of the corresponding intensity portions $I_1, I_2, I_3$, the individual intensity portions $I_1, I_2, I_3$ can be determined computationally therefrom using a corresponding normalization. This also preferably occurs via corresponding software in microprocessor FT.

Preferably, the individual modulations or the control signals $S_{f1}, S_{f2}, f_3$, and therewith also the radiation intensities $I_{01}$, $I_{02}$, or $I_{03}$ sent over time, have continuous curves, such as e.g. the sinusoidal curves illustrated here. This offers the advantage that hard@ turning on and off events and the occurrence of harmonic waves connected therewith are prevented on the transmission side.

Fundamentally, however, modulations with a rectangular shaped periodic curve can also be applied. In this case, the Fourier transformation offers the advantage that at least such harmonic waves that do arise can in given cases be subsequently eliminated; thus, the harmonic waves have different frequencies from the frequencies $f_1$, $f_2$, $f_3$ of the modulations.

Figure 3:
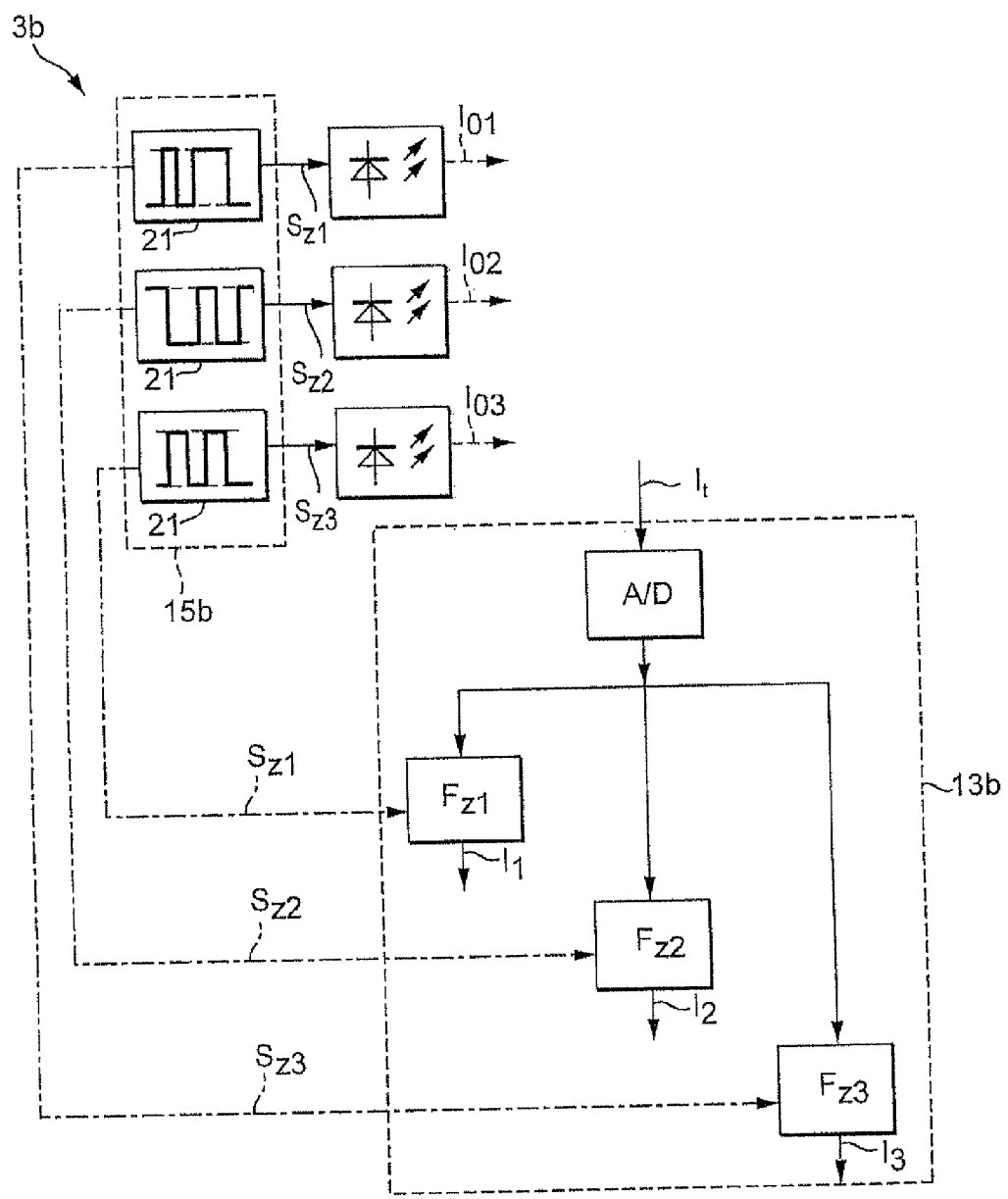
FIG. 3 is a transmission system and a signal processing system for an absorption measurement system according to FIG. 1 with non periodic modulation of the light sources.

FIG. 3 shows an example of an embodiment of the second variant of the invention with non periodic modulation of light sources L. Again, only the correspondingly embodied transmitting unit $3b$, the associated control $15b$, as well as the associated signal processing system $13b$ connected to amplifier circuit 11 of FIG. 1 are shown here. The remaining components can be assumed to be identical to those in FIG. 1. Also here, by way of example, three light sources $L_1$, $L_2$, $L_3$ of different wavelengths $\lambda_1, \lambda_2, \lambda_3$ are provided and the radiation intensities $I_{01}$, $I_{02}$, $I_{03}$ are modulated over time by means of a control $15b$ comprising three modules 21. Each module 21 produces a different non periodic control signal $S_{z1}$, $S_{z2}$, $S_{z3}$, preferably a randomly generated control signal, with which the radiation intensity $I_{01}$, $I_{02}$, $I_{03}$ of each light source $L_1$, $L_2$, $L_3$ connected thereto is modulated. The control signals $S_{z1}$, $S_{z2}$, $S_{z3}$ are, for example, rectangular pulses following one another; the duration of the rectangular pulses and/or the interval from one to another over time is determined by means of a random generator.

The processing of the reinforced measurement signal representing the total radiation intensity $I_t$ striking detector 5 also occurs here again preferably digitally based on the measurement signal digitized by the analog/digital converter A/D integrated in signal processing system $13b$ or connected in front of signal processing system $13b$.

The signal processing system $13b$ also determines the associated intensity portions $I_1$, $I_2$, $I_3$ here based on the different non periodic modulations for the individual wavelengths $\lambda_1$, $\lambda_2$, $\lambda_3$ and the digitized measurement signal.

For this, a digital filter $F_{z1}$, $F_{z2}$, $F_{z3}$, which filters out the signal components correlating with the associated modulation from the measurement signal, which is fed the digital measurement signal, is provided in each case for each wavelength $\lambda_1$, $\lambda_2$, $\lambda_3$, to be measured or for each of the different modulations. For this, the corresponding control signal $S_{z1}$, $S_{z2}$, or $S_{z3}$ is fed to each filter $F_{z1}$, $F_{z2}$, $F_{z3}$ via a connection with each associated module 21 of control $15b$. Then, for example, the fraction of the measurement signal correlating to the control signal $S_{z1}$, $S_{z2}$, $S_{z3}$ can be filtered out from the measurement signal in filters $F_{z1}$, $F_{z2}$, $F_{z3}$ via a convolution of the digital measurement signal with the associated control signal $S_{z1}$, $S_{z2}$, $S_{z3}$.

Since the ratio of the amplitudes of these fractions to one another corresponds to the ratio of the corresponding intensity portions $I_1$, $I_2$, $I_3$ to one another, the individual intensity portions $I_1$, $I_2$, $I_3$ can be computationally determined using a corresponding normalization. Preferably, this also occurs via corresponding software in a microprocessor.

Figure 4:
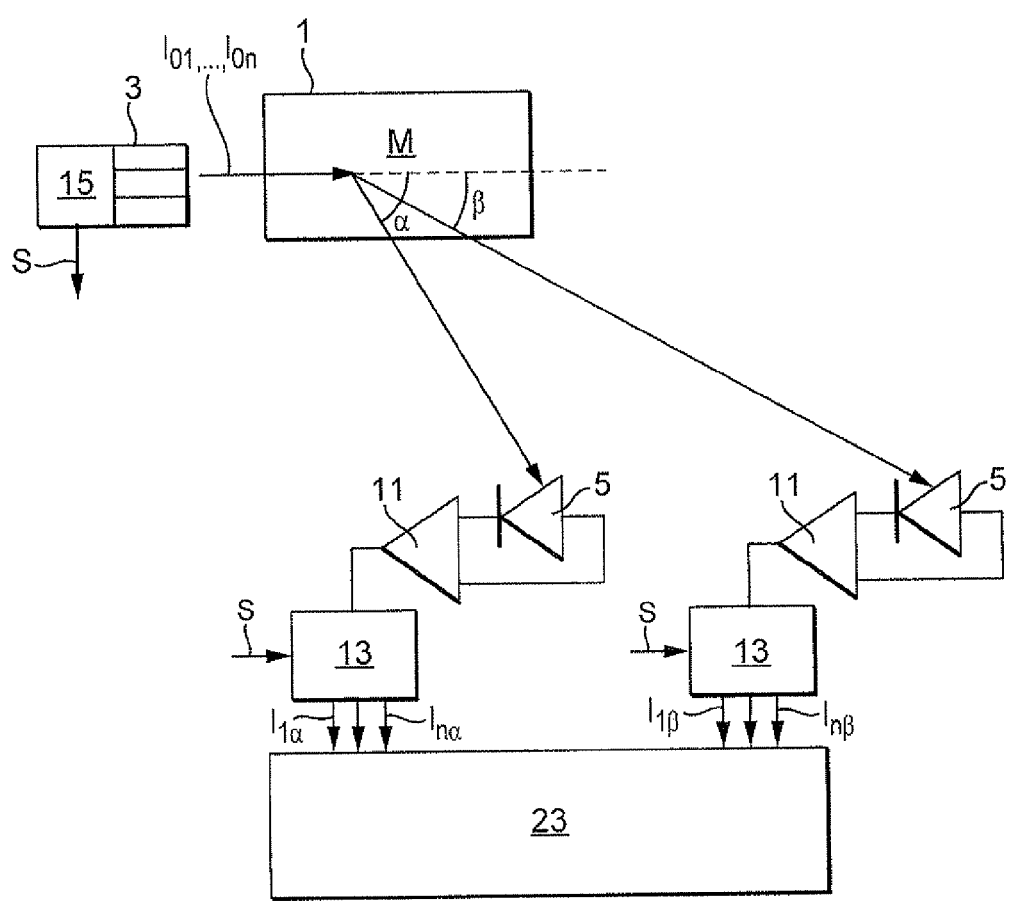
FIG. 4 is a scattering measurement system of the invention.

The invention is also completely analogously applicable in measuring systems for measuring the scattering of different wavelengths $\lambda_1, \lambda_n$ in a medium. An example is shown here in FIG. 4. Here again, light of different wavelengths $\lambda_1, \ldots \lambda_n$ is sent in a predetermined transmission direction into measuring chamber 1, which is filled with medium M. This occurs, exactly as in the described absorption measurement systems, by means of transmission system 3 and control 15 connected thereto, which operates the individual light sources $L_1, \ldots L_n$ with different time modulations of their transmission intensities $I_{01}, \ldots I_{0n}$ for each individual wavelength $\lambda_1, \ldots, \lambda_n$. The light is scattered in medium M, and the intensity portions $I_1 \ldots I_n$ of the individual wavelengths $\lambda_1, \ldots \lambda_n$ emerging from measuring chamber 1 at predetermined scattering angles $\alpha$, $\beta$ are measured. For this, a detector 5 arranged behind measuring chamber 1 in the transmission direction is provided for each scatter angle $\alpha$, $\beta$, at which there should be a measurement. Detectors 5 are identical to detector 5 of the described absorption systems, and for each scatter angle $\alpha$, $\beta$ the measurements of the intensity portions $I_1 \ldots I_n$ also occur in the same manner as in the absorption systems described. Correspondingly, an amplifier circuit 11 and a signal processing system 13 are also connected here to each detector 5. Also here, signal processing systems 13 transmit determined intensity portions $I_{1\alpha}, \ldots I_{n\alpha}$ and $I_{1\beta}, \ldots I_{n\beta}$ for each scatter angle $\alpha$, or $\beta$ to a measuring electronics 23, which determines the scattering for the individual wavelengths $\lambda_1, \ldots \lambda_n$ arising in the medium, and provides a display and/or an additional processing.

The invention claimed is:

1. A measuring system for measuring absorption or scattering of a medium at a plurality of different wavelengths, comprising:
   a measuring chamber for accommodating the medium;
   a transmitting unit, which has, for each wavelength, an electrically controllable light source, which sends light of its respective wavelength into said measuring chamber in measurement operation;
   a control, which operates each light source with a different time modulation of the transmission intensity for each wavelength,
   wherein the different modulations for the individual wavelengths have time curves such that, on average, an at least approximately constant number of light sources simultaneously send light into said measuring chamber in measurement operation at any given time;
   a detector for measuring a total radiation intensity dependent on the modulations and the absorption or the scattering in the medium and emerging from said measuring chamber at the site of said detector, the total radiation intensity corresponds to a superpositioning of each intensity portion striking said detector for each wavelength; and
   a signal processing system, which determines for each wavelength the associated intensity portion based on the total radiation intensity measured by said detector and the modulations.

2. The measuring system as claimed in claim 1, wherein:
   each of the light sources transmits light of its wavelength into said measuring chamber during predetermined transmission times with the time curve of the modulation used for its wavelength; and
   the transmission times of the light sources of different wavelengths overlap in time.

3. The measuring system as claimed in claim 1, wherein:
   the modulations are periodic modulations with predetermined different frequencies for the individual wavelengths.

4. The apparatus as claimed in claim 3, wherein:
   the modulations have continuous time curves.

5. The measuring system as claimed in claim 3, wherein:
   said signal processing system determines the intensity portions based on amplitudes of a Fourier transform of the measured radiation intensity arising from the predetermined frequencies of the associated modulation for each wavelength.

6. The measuring system as claimed in claim 1, wherein: the modulations are non periodic modulations.

7. The measuring system as claimed in claim 6, wherein:
said signal processing system has for each of the wavelengths a filter,
which filters from the measurement signal of said detector a fraction correlating with the time curve of the modulation for the particular wavelength; and
said signal processing system determines the associated intensity portion for this wavelength based on the respective fraction.

8. The measuring system as claimed in claim 1, further comprising:
transmission optics, via which the light from the light sources is sent into said measuring chamber along a predetermined transmission direction on a spatially limited measuring path; and/or
receiving optics, which focuses light escaping from said measuring chamber onto said detector.

9. The measuring system as claimed in claim 3, wherein the modulations have sinusoidal time curves.

10. The measuring system as claimed in claim 1, wherein the modulations are randomly generated modulations.

* * * * *